United States Patent [19]
Sater et al.

[11] Patent Number: 6,068,622
[45] Date of Patent: May 30, 2000

[54] SINGLE PIECE HUB/STRAIN RELIEF THAT CAN BE INJECTION MOLDED OVER A SHAFT

[75] Inventors: Ghaleb A. Sater, Lynnfield; Jeffrey J. Witts, Woburn; Raymond P. Knox, Worcester, all of Mass.

[73] Assignee: Medtronic Inc., Minneapolis, Minn.

[21] Appl. No.: 09/021,682

[22] Filed: Feb. 10, 1998

[51] Int. Cl.⁷ .................................................. A61M 25/00
[52] U.S. Cl. ........................................... 604/524; 604/527
[58] Field of Search ................................... 604/264, 523, 604/524, 534, 538, 527

[56] References Cited

U.S. PATENT DOCUMENTS

| | | |
|---|---|---|
| 3,618,613 | 11/1971 | Schulte . |
| 4,610,674 | 9/1986 | Suzuki et al. . |
| 4,636,346 | 1/1987 | Gold et al. . |
| 4,705,511 | 11/1987 | Kocak . |
| 4,806,182 | 2/1989 | Rydell et al. . |
| 4,875,481 | 10/1989 | Higgins . |
| 5,066,285 | 11/1991 | Hillstead . |
| 5,143,409 | 9/1992 | Lalikos . |
| 5,167,647 | 12/1992 | Wijkamp et al. . |
| 5,181,750 | 1/1993 | Reum . |
| 5,330,449 | 7/1994 | Prichard et al. . |
| 5,333,650 | 8/1994 | Folkham . |
| 5,380,301 | 1/1995 | Prichard et al. . |
| 5,466,230 | 11/1995 | Davila ................................ 604/264 X |
| 5,507,732 | 4/1996 | McClure et al. . |
| 5,509,910 | 4/1996 | Lunn . |
| 5,599,325 | 2/1997 | Ju et al. ............................... 604/264 X |
| 5,676,659 | 10/1997 | McGurk . |

OTHER PUBLICATIONS

SciMed ST 55cm (806 EOL 777) at 150% lifesize—Guiding Catheter.
SciMed Maxxum Catheter Manifold Photograph and Instructions for use Aug. 19, 1996.
Sealcon or Hummel Liquid Tight Strain Relief Fittings and Flexible Conduit System for Cable and Wire.
Sealcon: Liquid Tight Strain Relief Fittings and Flexible Conduit System for Cable and Wire, 1989.

*Primary Examiner*—Wynn Wood Coggins
*Assistant Examiner*—A. T. Nguyen

[57] ABSTRACT

Medical vascular catheters adapted to be inserted into a blood vessel from an incision through the skin of a patient for introducing other devices or fluids for diagnostic or therapeutic purposes into the patient's vasculature and manufacturing methods are disclosed. The catheters have a unitary catheter hub and strain relief formed at the proximal end of the catheter body for attachment to other apparatus and for inhibiting kinking of the catheter body. The unitary catheter hub and strain relief is formed of a proximal hub portion and a distal strain relief coil surrounding the catheter body in a catheter hub/body junction. The distal strain relief coil is shaped as a distally tapered, single coil to provide distally increasing flexibility and uniform bending characteristics in 36° around the circumference of the catheter body received within the within the strain relief coil lumen. The strain relief coil is optionally formed with blends of materials selected to distally increase the distal strain relief bending flexibility.

21 Claims, 5 Drawing Sheets

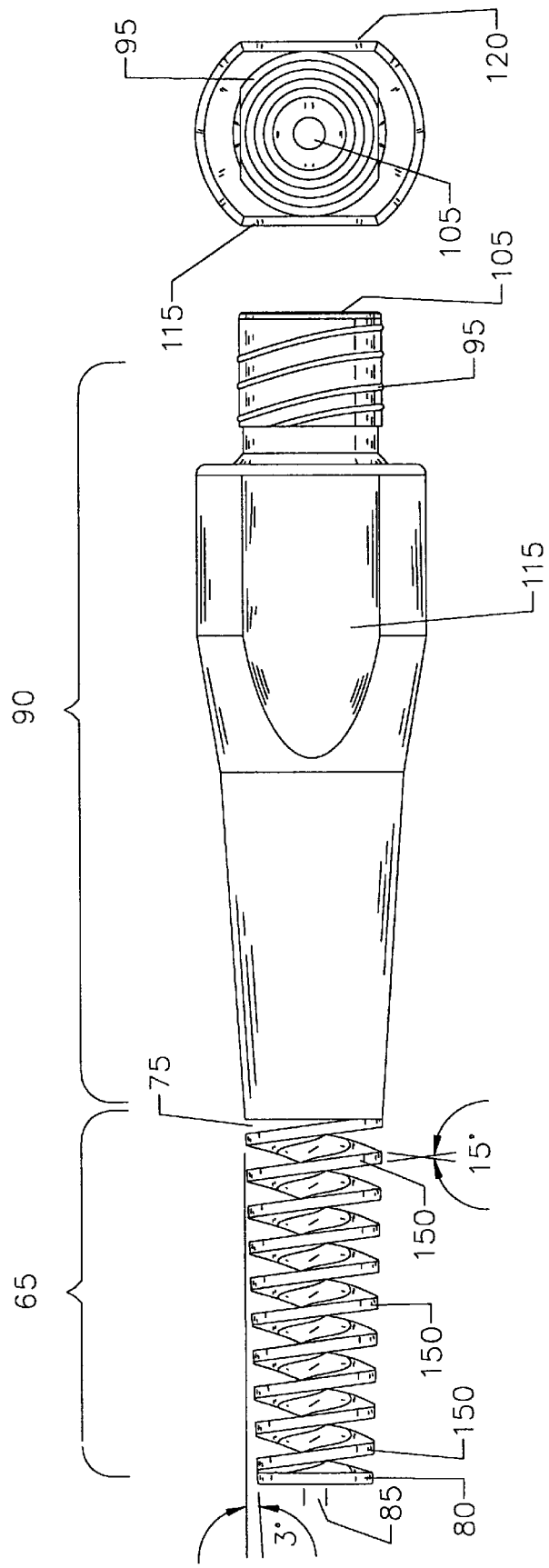

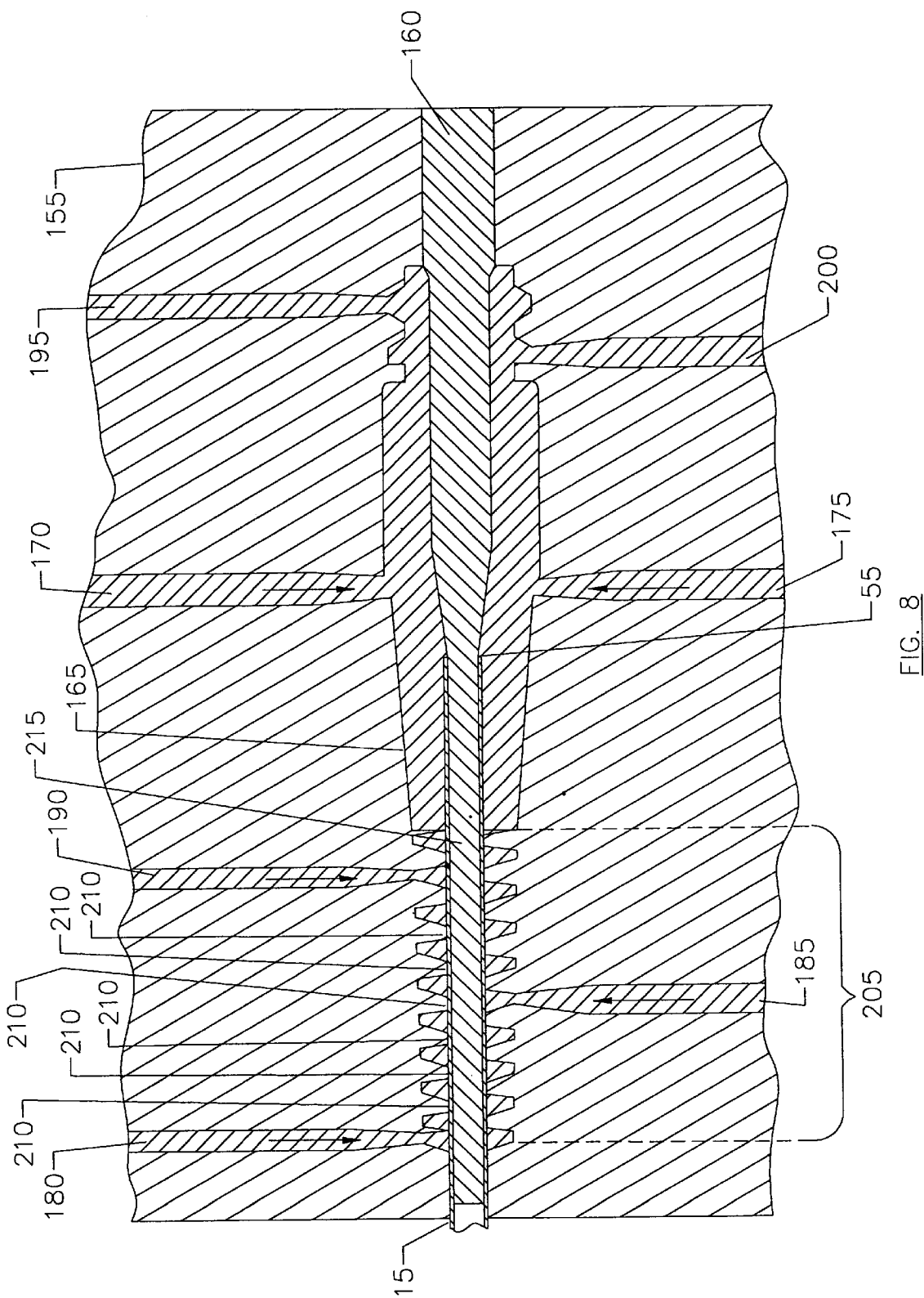

SINGLE PIECE HUB/STRAIN RELIEF THAT CAN BE INJECTION MOLDED OVER A SHAFT

FIELD OF THE INVENTION

The present invention relates to medical vascular catheters adapted to be inserted into a blood vessel from an incision through the skin of a patient for introducing other devices or fluids for diagnostic or therapeutic purposes. More particularly, the present invention is directed to a unitary catheter hub and strain relief formed at the proximal end of the catheter body for attachment to other apparatus and for inhibiting kinking of the catheter body and a method of manufacture and attachment of the catheter hub and strain relief to the catheter body.

BACKGROUND OF THE INVENTION

Medical vascular catheters are particularly designed and available for a wide variety of purposes, including diagnosis, interventional therapy, drug delivery, drainage, perfusion, and the like. Medical vascular catheters for each of these purposes can be introduced to numerous target sites within a patient's body by guiding the catheter through an incision made in the patient's skin and a blood vessel and then through the vascular system to the target site.

Medical vascular catheters generally comprise an elongated, flexible catheter tube or body with a catheter side wall enclosing a catheter lumen extending between a catheter body proximal end coupled to a relatively more rigid catheter hub to a catheter body distal end. The catheter body may be relatively straight or inherently curve or curved by insertion of a curved stiffening wire or guide wire through the catheter lumen. The catheter body and catheter side wall are typically fabricated and dimensioned to minimize the catheter body outer diameter and side wall thickness and to maximize the catheter lumen diameter while retaining sufficient side wall flexibility and strength characteristics to enable the catheter to be used for the intended medical purpose.

The catheter hub functions as a connector to allow quick connection of a syringe or the like with the catheter lumen. The catheter body distal end may be formed with one or more side wall opening formed in a segment typically adjacent the catheter body distal end and/or with a distal end opening axially aligned with the catheter body. Or the catheter body may additionally or alternatively have further structure formed on the catheter body side wall, e.g., an expandable balloon for dilatation of a blood vessel or installation of an expandable stent or graft, or a sensor, or a therapeutic or diagnostic device. Moreover, the catheter body may include two or more catheter lumens communicating with access ports formed in or extending from the catheter hub to such opening(s) or structure(s).

Often much manipulation is required to guide such catheters through the incision and/or introducer lumen and then through the vascular system to the target site in the body to effect the medical procedure. This manipulation is effected by grasping the catheter body and/or the catheter hub extending outside the body and pushing and twisting it to advance the catheter body distal end through twists and turns of the blood vessel. This manipulation strains and stresses the catheter body, particularly at the catheter body proximal end where the relatively flexible and thin catheter side wall exits from a hub lumen.

Further, the introduction of the vascular catheter into the vascular system may not be the time at which the greatest strain is placed on the catheter hub/body junction. Often, after the catheter body is fully advanced to the target site, the healthcare provider will raise the catheter hub away from the patient's skin in order to insert a smaller catheter or guide wire or the like or a syringe into the hub lumen proximal end opening or to connect a further device to the hub fitting. This raising of the catheter hub places a large bending strain on the catheter hub/body junction, and the catheter body can bend sufficiently to buckle or kink in this area as a result. Or, in a chronic implantation, such kinking can occur at the catheter hub/body junction when the patient rolls over in bed.

In one approach, the hoop strength of the catheter body is maximized at least in a proximal segment thereof. However, this approach stiffens the catheter body and can require a reduction in the catheter lumen diameter. If the full length of the catheter body is stiffened to make it more resistant to kinking, then the stiffness can make the catheter body less maneuverable, particularly in tortuous pathways and through small blood vessels and can cause damage to the vessel walls. A great deal of effort has been expended in developing catheter side walls trading off factors of hoop strength, flexibility catheter body outside diameter, side wall thickness, etc., that affect flexibility, column strength, and maneuverability, and still resist catheter body kinking and minimize damage to blood vessel walls. For example, as described in U.S. Pat. No. 5,066,285, the tubular sheath of a catheter sheath introducer is made of expanded, fibrous polytetrafluoroethylene (PTFE) so as to produce a more flexible sheath having a high hoop strength that allegedly resists kinking. In U.S. Pat. No. 3,618,613, related to a drainage catheter not intended to be inserted through a blood vessel. the tube side wall is reinforced by an embedded wire spring coil. Similarly, uses of embedded wire spring coils to reinforce a medical vascular catheter are disclosed in U.S. Pat. Nos. 4,634,342 and 4,705,511. These reinforced catheter sheaths are helpful in situations where the advancement causes the strain, such as when introducing the catheter through scar tissue. Specialized catheter bodies fabricated to solve the tendency of the catheter body to kink at the catheter hub/body junction are often more difficult to produce and costly to manufacture than uniform catheter bodies.

Despite these efforts, a strain relief is usually incorporated into the catheter hub/body junction in an effort to prevent such kinking of the catheter side wall during installation and use as shown, for example, in U.S. Pat. No. 5,599,325. Strain reliefs are traditionally formed of a bridging material that is more flexible than the catheter hub and less flexible than the catheter body and surrounds a proximal segment of the catheter body to reinforce it. The strain relief is typically attached at the proximal strain relief end to the catheter hub and extends along the proximal catheter body segment to a distal strain relief end. The object of the strain relief is to prevent concentration of the bending forces at the catheter hub/body junction by resisting and dissipate applied bending forces along the length of the strain relief, and thereby prevent collapse of the catheter side wall and kinking of the catheter body. The strain relief thereby functions to "relieve" the strain at the catheter hub/body junction by spreading bending forces along a larger length of the catheter body.

The bending force and kinking problems are described in U.S. Pat. Nos. 5,167,647, 5,330,449, and 5,380,301 for example, incorporated herein by reference, and addressed by use of tubular sheath strain reliefs surrounding and extending distally from the catheter hubs. In the '301 patent, the strain relief is incorporated with a locking mechanism that is alleged to reduce or eliminate any tendency of the release of the catheter hub from the catheter body proximal end due to excessive force applied axially between them. Similar tubular strain reliefs are disclosed in U.S. Pat. No. 5,507,732 and in the above-referenced '325 patent. The tubular sheath strain relief may be tapered from the proximal strain relief end to the distal strain relief end to increase flexibility distally.

Alternatively, the use of coil springs having a spring lumen receiving a distal segment of the catheter body have been disclosed in U.S. Pat. Nos. 4,610,674 and 5,466,230, for example. At least the proximal section of the coil spring disclosed in the '230 patent and the entire length of the coil spring disclosed in the '674 patent are embedded within a tubular sheath or the strain relief. As noted in the '230 patent, the coil spring can either be square or round and formed of a metal or plastic material. In both cases, the coil wire diameters are constant through the length of the coil spring.

In a further approach, convoluted plastic strain reliefs have been incorporated into vascular catheters sold by SciMed Life Systems, Minneapolis, Minn., (an affiliate of Boston Scientific Co.) under the trademarks "Cyber" and "Wiseguide". In these SciMed Cyber and Wiseguide guide catheters, the strain relief takes the form of a series of rings formed around the catheter body and extending along a proximal segment thereof that have ring diameters that decrease distally. The rings are spaced apart from one another but connected with one another at points, e.g., at 180°, around the circumference of the catheter body by bridging elements. The strain relief thus resembles a common strain relief used on computer keyboard cables. This type of strain relief does not afford a uniform degree of flexion and kinking resistance around the entire 360° circumference of the catheter body surrounded by it. The bridging elements distort the bending flexibility so that the strain relief bends more readily when bent at 90° to each such bridging elements.

It is therefore well known that the catheter hub/body junction is highly susceptible to strain due to intentionally or inadvertently applied bending forces and that a wide variety of strain reliefs have been employed in the attempt to address this problem. Despite the considerable effort in designing strain reliefs at the catheter hub/body junction, problems still occur with kinking of the catheter body either within the length of the strain relief or just distally to the distal strain relief end.

SUMMARY OF THE INVENTION

It is an object of the invention to provide a unitary catheter hub and strain relief that overcomes these problems, and provides superior and uniform flexibility and resulting bending characteristics around the full 360° circumference of the catheter body at all points along the length of the strain relief.

It is a further object of the invention to provide such a unitary catheter hub and strain relief that can be readily tailored in dimensions and flexibility and bending characteristics to match the construction, dimensions and bending and crush resistance characteristics of the catheter body.

It is yet another object of the invention to provide superior adhesion between the unitary catheter hub and strain relief and the outer surface of the catheter body along the length of the catheter hub/body junction.

It is a still further object of the invention to provide a unitary catheter hub and strain relief that is inexpensive to manufacture.

These and other objects of the present invention are realized through the formation of a unitary catheter hub and strain relief about and adhered to a proximal portion of the catheter body in an elongated catheter hub/body junction thereof, the unitary catheter hub and strain relief having a proximal hub portion and a strain relief coil formed integrally with a distal end of the proximal hub portion and extending distally therefrom in a coil length between a proximal strain relief coil end and a distal strain relief coil end and surrounding a strain relief coil lumen receiving the proximal portion of the catheter body, the proximal hub portion having a distal hub lumen portion aligned axially with the strain relief coil lumen for receiving the proximal portion of the catheter body in an elongated catheter hub/body junction, the strain relief coil formed of a plurality of spiral turns separated from one another by an interleaved spiral-shaped spacing and providing a uniform bending flexibility around the 360° circumference of the catheter body that increases distally through the length of the strain relief coil.

The proximal portion of said catheter body is preferably formed of an outer tubular sheath, an inner tubular sheath, and a wire braid tube sandwiched between the outer and inner tubular sheathes and has a side wall crush resistance of about 2–7 pounds.

The unitary catheter hub and strain relief is preferably formed by injection molding of a thermoplastic material around the proximal portion of the catheter body. The thermoplastic materials of the unitary catheter hub and strain relief and the outer tubular sheath of the catheter body are selected to be compatible with one another and to form a bond during the injection molding process. The proximal portion of the catheter body is supported within and preheated in the injection mold to soften or melt the outer layer or sheath thereof. The injected thermoplastic material and the melted or softened material of the outer layer or sheath then form a bond having high adhesion strength and resistance to axially applied forces after the injected material solidifies and the assembly is removed from the injection mold.

The progressive or graduated distally increasing flexibility through the length of the strain relief coil is effected by the pitch and distally decreasing outer diameter of the strain relief coil but can also be effected by molding the strain relief coil of blends of selected thermoplastic materials exhibiting progressively decreasing Shore D hardness distally from the integral junction with said proximal hub portion. The hardness of the The practice of the method of the present invention forming the unitary catheter hub and strain relief around the catheter body along the length of the catheter hub/body junction in a single molding step reduces fabrication costs and provides for enhanced adhesion therebetween. Small scale injection molding techniques can be advantageously employed that reduces the manufacturing equipment cost and the space required to complete the fabrication of the unitary catheter hub and strain relief about the catheter body.

The enhanced adhesion particularly in the spiral surface junction of the strain relief coil with the outer surface or layer of the catheter body increases the amount of axial force required to be applied along the longitudinal axis of the catheter body to pull it out of the lumen of the unitary catheter hub and strain relief. Such longitudinal ("pulling") forces can arise during the use of a catheter through any number of commonly occurring accidents or mishaps, and can lead to disastrous consequences for a patient who may heavily rely on the proper functioning of the catheter.

The unitary catheter hub and strain relief molded about the proximal portion of the catheter body provides superior and uniform flexibility and resulting bending characteristics around the full 360° circumference of the catheter body at all points along the length of the strain relief.

The unitary catheter hub and strain relief of the present invention that can be readily tailored in dimensions and flexibility and bending characteristics to match the construction, dimensions and bending and crush resistance characteristics of the catheter body. The overall length of the molded strain relief coil can be minimized while providing the superior and uniform bending characteristics about the full circumference of the catheter body Moreover, through the selection of the pitch and dimensions of the strain relief coil, graduated bending flexibility that increases distally can be effected along the length of the catheter hub/body junction within the strain relief coil lumen.

In addition, bending characteristics of the strain relief coil and flexibility of the hub portion can be tailored through the selective use of differing Shore hardness thermoplastic material blends to mold the strain relief coil and the hub portion.

BRIEF DESCRIPTION OF THE DRAWINGS

FIG. 6 is an enlarged plan view of the unitary catheter hub and strain relief of the preferred embodiment;

FIG. 7 is an end view of the hub portion of the unitary catheter hub and strain relief of the preferred embodiment; and FIG. 8 schematically illustrates an exemplary method of manufacturing the unitary catheter hub and strain relief of the preferred embodiment over and adhered with the proximal segment of the catheter body.

DETAILED DESCRIPTION OF THE PREFERRED EMBODIMENTS

The present invention provides an improved construction for catheters of the type having an elongated catheter body with at least one catheter lumen extending from catheter body proximal end to a catheter body distal end thereof. Such constructions are particularly useful for forming medical vascular catheters in a wide range catheter body lengths and outer diameters. Such catheters include small diameter vascular catheters, having catheter body outside diameters of 4 mm (12 F) preferably below 2.67 mm (8 F), and frequently as small as 1 mm (3 F), and below, such as those used in neurological diagnostic and interventional procedures. Such small diameter vascular catheters will also be useful for other procedures, such as gynecological procedures, cardiac procedures, general interventional radiology procedures, and the like, for access to the small vasculature as necessary. Constructions of the present invention, however, are not limited to such small diameter catheters, and will be useful for larger diameter catheters as well, such as vascular guiding catheters and PTCA balloon catheters which may have outside diameters larger than 4 mm.

Medical vascular catheters according to the present invention will comprise a catheter body having dimensions, a particular side wall construction and a geometry selected for the intended use. The catheter body will typically have a length in the range from about 40 cm to 200 cm, usually having a length in the range from about 60 cm to 175 cm. The outside diameter of the catheter body will typically be in the range from about 0.33 mm (1 F) to 4 mm (12 F), usually being in the range from about 0.66 mm (2 F) to about 3.33 mm (10 F). The catheter body will define an inner lumen typically having a diameter in the range from about 0.1 mm to 3.6 mm, usually being in the range from about 0.3 mm to 3.0 mm, with catheters having larger outside diameters usually having larger catheter lumen diameters.

Figure 1:
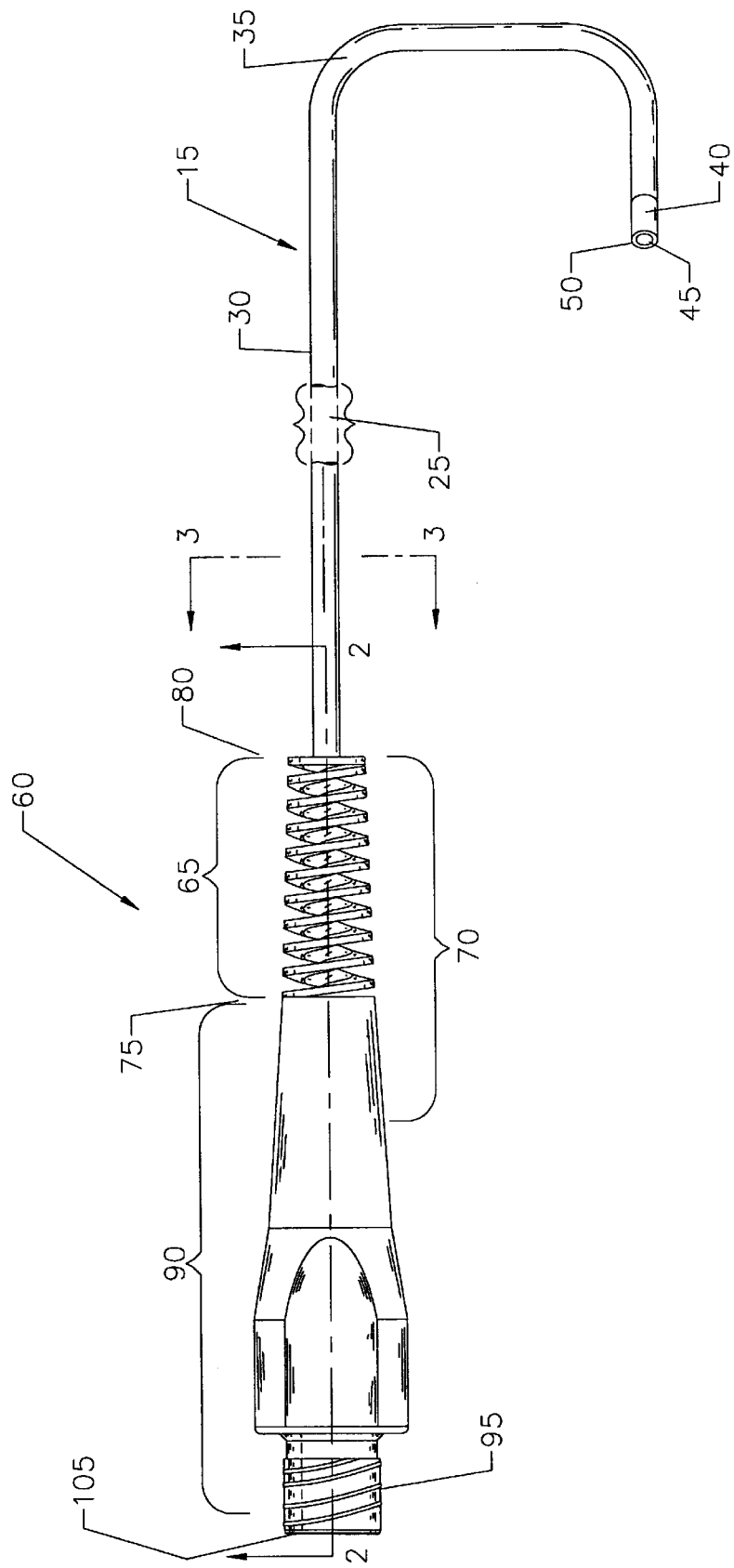
FIG. 1 is a plan view of an exemplary medical vascular catheter constructed with the unitary catheter hub and strain relief in accordance with a preferred embodiment of the invention.
Figure 2:
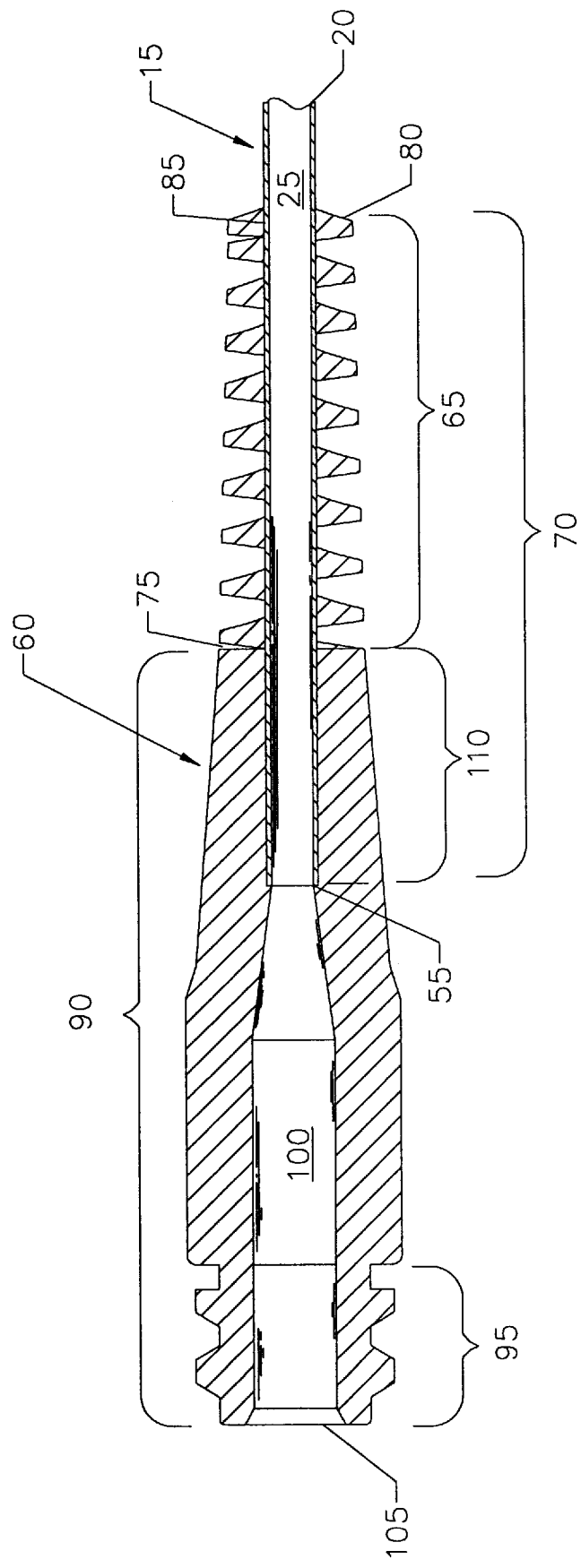
FIG. 2 is an enlarged cross-section view of the unitary catheter hub and strain relief adhered with a proximal segment of the catheter body taken along lines 2—2 in FIG. 1.

FIG. 1 is a plan view of an exemplary medical vascular catheter 10 constructed with the unitary catheter hub and strain relief 60 receiving the catheter body 15 and attached to the catheter body proximal end 55 as shown in FIG. 2 in accordance with a preferred embodiment of the invention The catheter body 15 will usually be straight along all or most of its length, that is it will assume a straight or linear configuration, when free from external bending forces. The catheter body 15, however, will be highly flexible so that it will be able to pass through the tortuous regions of a patient's vasculature. In some cases, the catheter body 15 may have a shaped distal end segment including curves and bends which are selected to facilitate introduction and placement of the catheter 10 (usually over a separate guide wire) in the vascular system. A particular geometry of curves and/or bends may be selected to accommodate the intended use of the catheter 10.

In one typical application of the invention, the catheter body 15 will usually include at least two, and sometimes three or more distinct segments or regions, with each segment having a different construction resulting in different mechanical properties. A proximal region 30 may extend from the catheter body proximal end 55 to a location spaced within 20 cm of the catheter body distal end 50, usually from 2 cm to 6 cm of the catheter body distal end 50. The proximal region 30 will have the maximum reinforcement of the catheter body 15, thus having most column strength and hoop strength, but the least flexibility. In accordance with the three region embodiment, the proximal region 30 is formed of the inner tubular sheath 125, outer tubular sheath 130 and a wire braid tube 135 sandwiched between the inner and outer tubular sheathes 125 and 130 as described below.

In the three region embodiment, a transition region 35 is located immediately distally of the proximal region 30 and extends to a location spaced within 30 cm of the catheter body distal end 50, usually from 1 cm to 3 cm of the catheter body distal end 40. The transition region 35 has an intermediate level reinforcement providing an intermediate level of column strength, hoop strength, and flexibility. A distal "soft tip" region 40 extends distally from the transition region 35, and is composed of a soft, un-reinforced material. The distal soft tip may be formed in the manner described in the above-incorporated, commonly assigned U.S. Pat. No. 5,509,910. The distal region 40 will generally be relatively short, typically having a length in the range from about 1.0 mm to 3.0 cm, and will have the greatest flexibility of the three regions of the catheter body 15. In a first alternate embodiment, the transition region 35 is eliminated, and the distal soft tip region is formed as described above.

Figure 4:
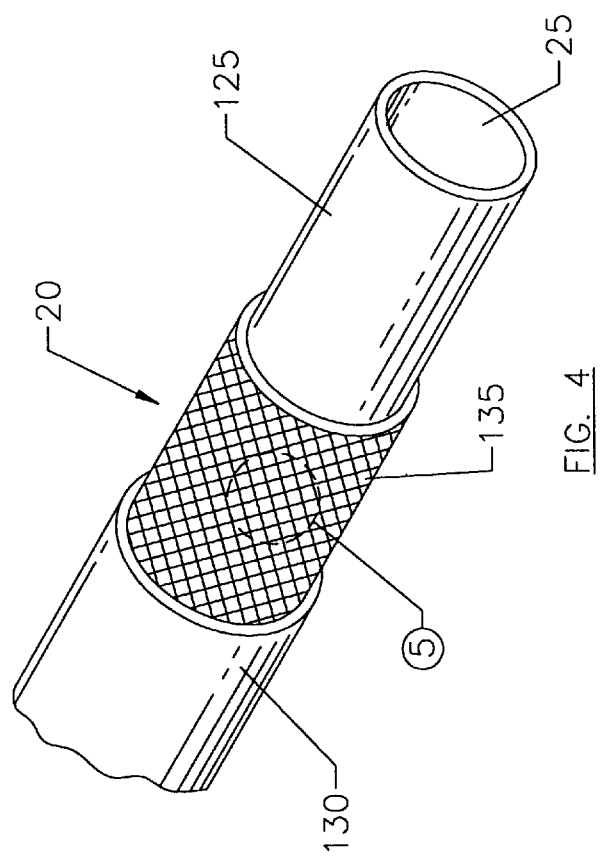
FIG. 4 is a perspective view of a section of the catheter body peeled back to reveal an inner tubular sheath, an outer tubular sheath and a wire braid tube sandwiched between the inner and outer tubular sheathes.
Figure 5:
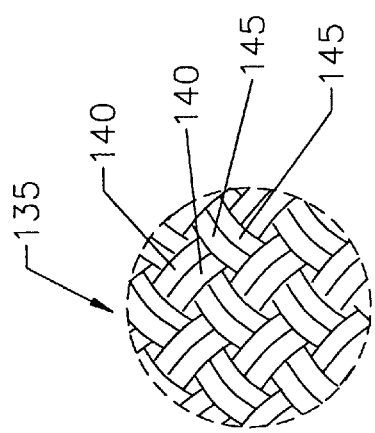
FIG. 5 is an magnified view of the wire braid of the wire braid tube of FIG. 4.
Figure 3:
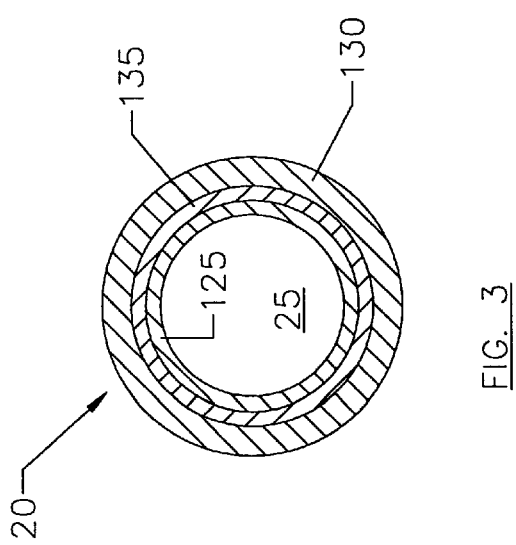
FIG. 3 is an enlarged cross-section view of the catheter body taken along lines 3—3 in FIG. 1.

A preferred embodiment of the construction of the catheter body 15 is depicted in FIGS. 3–5. The catheter body 12 is preferably formed in the manner taught in commonly assigned U.S. Pat. Nos. 5,566,659 and 5,509,910, both incorporated by reference herein. In accordance with the preferred embodiment of the invention, at least the proximal region is formed of an outer tubular sheath 130, an inner tubular sheath 125 and a wire braid tube 135 sandwiched between the outer and inner tubular sheathes 130 and 125.

Typically, the inner tubular sheath 125 is formed from a single material, preferably a lubricious polymer, such as a fluorocarbon (e.g., polytetrafluoroethylene (PTFE)), a polyamide (e.g., nylon), polyether block copolyamides (PEBA), a polyolefin, a polyimide, or the like. It would also be possible to form the inner tubular sheath 125 as a laminate structure comprising a non-lubricious outer layer and an inner lumen surrounding layer or coating of a more lubricious material.

The wire braid tube 135 comprises "warp" and "woof" wire filament pairs 140 and 145 braided in a fabric basket weave pattern wound to form a tube. The wire braid tube 135 may be woven directly over the inner tubular sheath 125 using conventional fabric weaving techniques. Or, the wire braid tube 135 may be woven over a mandrel using conventional braiding techniques and then fitted over the inner tubular sheath 125, In either case, the outer tubular sheath 130 is then fitted over the wire braid tube 135. The wire filament pairs 140 and 145 have a very small cross-sectional area while possessing sufficient tensile strength to undergo the braiding process.

Preferably, round wire filaments of stainless steel, a shape memory alloy (e.g., Nitinol), polymeric fibers, or the like, are used. Stainless steel filaments having a round cross-section with a diameter in the range from 0.001 inch to 0.01 inch, preferably about 0.023 inches are particularly preferred. Such small filaments can be formed into the wire braid tube 135 over a tubular support member in a conventional one-over-one or two-over-two braid pattern, with the machine being carefully adjusted to avoid excessive tensile forces on the filaments.

The outer tubular sheath 130 is preferably formed of a variety of materials, preferably being composed of a soft thermoplastic material having a hardness in the range from 30 Shore A to 72 Shore D. Exemplary materials include polyamide polyether block copolyamides (PEBA), polyurethanes, silicone rubbers, nylons, polyethylenes, fluorinated hydrocarbon polymers, and the like.

A proximal region 30 of the catheter body 15 constructed in this manner having an outer diameter of about 0.106 inches and a catheter lumen inner diameter of about 0.088 inches has a hoop strength or crush resistance to a load of 2–7 pounds applied perpendicular to its longitudinal axis. The catheter body also exhibits an elastic modulus of between 28,000 psi and 40,000 psi under standard axial load conditions. The catheter body formed of the outer, inner and wire braid intermediate sheathes also has a kink resistance which enables it to withstand a loadt of 0.5 pounds moment weight for a minimum deflection of 30° before the side wall kinks.

Referring again to FIGS. 1 and 2, the catheter 10 constructed in accordance with the principles of the present invention includes the unitary catheter hub and strain relief 60 that receives and is attached with a proximal segment of the catheter body 15. The proximal segment extends distally from the catheter body proximal end 55 through and defining the length of a catheter hub/body junction 70. The unitary catheter hub and strain relief 60 is injection molded as a single piece over the catheter hub/body junction 70 as described below in reference to FIG. 8.

The unitary catheter hub and strain relief 60 is formed of a proximal hub portion 90 that is integrally connected to the proximal strain relief coil end 75 of the strain relief coil 65. The strain relief coil 65 is a continuous coil of constant or variable pitch having coil turns that decrease in diameter from the proximal strain relief coil end 75 to the distal strain relief coil end 80.

The turns of the strain relief coil 65 are preferably molded over a distal portion of exterior surface of the catheter body 15 in the catheter hub/body junction 70 and adhered in a spiral pattern to the exterior surface of the catheter body. In this manner, a strain relief coil lumen 85 is effectively formed because the distal portion of exterior surface of the catheter body 15 extending the length of the catheter hub/body junction 70 functions as a mandrel.

The hub portion 90 surrounds and defines a hub lumen 100 extending from the hub lumen proximal end opening 105 to the proximal strain relief coil end 75. The circular hub lumen 100 has a maximum diameter at the hub lumen proximal end opening 105 and has a progressively decreasing diameter to the proximal end of the catheter hub/body junction 70 where the hub lumen 100 is slightly increased in diameter to that of the outer diameter of the catheter body 15. The unitary catheter hub and strain relief 60 is injection molded as a single piece over a proximal portion of the catheter body 15 in the catheter hub/body junction 70. Therefore, the distal hub lumen portion 110 of the hub lumen 100 extends over a proximal portion of the catheter hub/body junction 70 is filled with the catheter body 15. The proximal portion of the hub lumen 100 and the hub lumen end opening 105 are formed in the injection molding process by use of a mandrel shaped so that an annular step or shoulder of a width corresponding to the thickness of the catheter body side wall 20 is formed abutting the catheter body proximal end 55. In this way, the diameter of the hub lumen 100 is made equal to the diameter of the catheter lumen 25 at the catheter body proximal end 55. In the preferred molding process, the material of the unitary catheter hub and strain relief 60 is molded over a proximal portion of the catheter body 15 over the length of the catheter body 15 through the catheter hub/body junction 70 by the strong adhesion to the exterior surface of the outer tubular sheath 130. This adhesion prevents the catheter body from being pulled away from the unitary catheter hub and strain relief 60 by longitudinally applied force.

FIGS. 6 and 7 more clearly reveal details of the shape of the unitary catheter hub and strain relief 60. The hub portion 90 includes the hub fitting 95 which is a standard, threaded ISO 594-½ fitting for attaching a variety of devices to it. The circular hub lumen end opening 105 is also adapted to receive a syringe needle or the like. A pair of oppositely disposed hub flats 115 and 120 are provided for grasping the unitary catheter hub and strain relief 60 during introduction and manipulation as described above. It will be understood that the depicted hub portion 90 and hub fitting 95 are simply exemplary, and that they may take any of the known forms and shapes for medical vascular catheters.

The spiral strain relief coil 65 and a distal portion of the exterior surface of the hub portion 90 have a circular profile and are tapered distally at a common angle of 2.5°–3.5° with respect to the aligned longitudinal axes of hub lumen 100 and strain relief coil lumen 85. In addition, the spiral turns 150 of the strain relief oil are tapered on each side of each turn at about ±82.5° to the longitudinal axis of the strain relief coil lumen 85 to form about a 15° inclusive angle and a trapezoidal profile in a cross-section view of each spiral turn. In this manner, it can be seen that the strain relief coil 65 is formed of a plurality of spiral turns 150 separated from one another by an interleaved spiral-shaped spacing. The final spiral turn is formed into a ring at the distal strain relief coil end 80.

Because of the tapered, non-parallel sides of the trapezoidal cross-section spiral turns 150, the spiral turns have a torsional twist or preload of approximately 1°–5° along the length of the strain relief coil 65. The torsional twist or preload causes the spiral turns 150 to become locally strained hardened when a lateral deflection or bend is formed in the strain relief coil 65 and the underlying catheter body 15 by flexural displacement of the distal strain relief coil end 80. The local strain hardening increases the flexural stiffness of the strain relief coil 65 as the bend is increased by further flexural displacement of the distal strain relief coil end 80. It is believed that the ability of the strain relief coil 65 to increase its effective flexural modulus as the lateral deflection or bend increases results in improved resistance to bend kinking in the region of the catheter hub/body junction 70 as compared to prior art catheter strain reliefs.

These angles can be modified as found desirable to impart a bending flexibility to the assembly over the length of the catheter hub/body junction 70. The width of the spiral coil base adhered to the outer surface of the outer tubular sheath 130 can be maintained constant through the length of the strain relief coil 65 or can diminish distally through all or part of the length of the strain relief coil 65. Similarly, the coil pitch can be constant or it can be varied through the length of the strain relief coil, thereby stepwise or continuously changing the distance between adjacent coil turns. Thus, the flexibility of the strain relief coil 65 can be increased distally by selected adjustments of one or more of these parameters FIG. 8 schematically illustrates an exemplary method of molding the unitary catheter hub and strain relief 60 of the preferred embodiment over and adhered with the proximal catheter hub/body junction 70 in an injection mold 155 of a type well known in the art. Injection mold 155 is shown in cross-section to reveal the mold cavity 165 that is dimensioned in a spiral turn section 205 to receive a proximal portion of the proximal region 30 in the distal portion of the catheter hub/body junction 70. The spiral turn section is shaped and dimensioned as described above to form the spiral strain relief coil 65. The mold cavity 165 is also shaped in the proximal portion thereof to receive a tubular mandrel 160 which is shaped and dimensioned to define the hub lumen 100 between the hub lumen end opening 105 and the catheter body proximal end 55. The distal extension 215 of the tubular mandrel 160 is shaped as a rod having an outer diameter sized with respect to the inner lumen diameter of the catheter lumen 25 so that the catheter body 15 can be fitted over it. The distal extension 215 therefore supports the side wall of the catheter body during the injection of the thermoplastic material and maintains the catheter body 15 centrally disposed within the mold cavity 165. The tubular mandrel 160 is also supported at its proximal end in each half of the injection mold 155 so that it is centrally disposed in the mold cavity 165.

A plurality of sprues 170,175,180, 185,190,195 and 200 (or a lesser or greater number of such sprues) extend between feed line fittings (not shown) outside the mold 155 and to injection ports or gates spaced along the mold cavity 165. Smaller sized vents (not shown) may also extend through the injection mold 155 between the mold cavity 165 and the atmosphere to allow escape of air in the mold cavity 165 during the injection process. Runners may extend between certain or all of the sprues 170–200 depending on whether a single thermoplastic material is injected or if differing hardness blends of the thermoplastic material are selectively injected as described below.

The injection mold 155 may be machined of two half sections of metal stock in order to form the mold cavity 165 and in order to be opened to receive the other components illustrated in FIG. 8 and to withdraw the finished assembly. In use, the proximal portion of the proximal region 30 of the catheter body 15 is fitted over the distal extension 215, and the tubular mandrel 160 is fitted within mold cavity 165. These components are assembled as depicted in FIG. 8 within the mold cavity 165, and the half sections of the mold 155 are fitted and secured together.

The assembled injection mold 155 is heated in order to preheat the outer surface of the catheter body 15 so that a secure adhesion is effected with the injected thermoplastic material. In this regard, the spiral turn section 205 constitutes a continuous spiral mold cavity section that receives and distributes the injected thermoplastic material to form the strain relief coil 65. The spiral turn section 205 also is shaped to form the flattened spiral heating element having adjacent heating element turns 210 that bear against the outer surface of the catheter body 15. Heat applied through the heating element turns 210 is conducted through the catheter body 15 between each adjacent heating element turn 210. The applied heat softens or melts the outer surface of the catheter body, e.g., the outer tubular sheath 130 in the preferred embodiment. The plurality of sprues 170–200 are coupled to a source of molten plastic, and the molten plastic is injected at a suitable pressure and for a duration sufficient to fill all of the space within the mold cavity 165 and any of the vents. Strong adhesion of the injected thermoplastic material with the outer surface of the tubular body 15 is effected. After a short cooling period, the mold 155 is opened so that the assembly can be manually withdrawn or ejected. The tubular mandrel 160 is withdrawn, and the sprue and vent runners are trimmed away. Of course the component assembly, injection and ejection steps of the process can be automated.

In this manner, the spiral strain relief coil 65 and the hub portion 90 are formed as the unitary catheter hub and strain relief 60 of the preferred embodiment. The materials that may be injected into the mold cavity 165 in this manner to form the unitary catheter hub and strain relief 60 preferably include the same materials that are specified for the outer tubular sheath polyamide polyether block copolyamides (PEBA), polyurethanes, silicone rubbers, nylons, polyethylenes, fluorinated hydrocarbon polymers, and the like. Like materials are selected that melt together to form the strong bond between unitary catheter hub and strain relief 60 including the strain relief coil 65 with the catheter body 15 along the length of the catheter hub/body junction 70.

Although a single thermoplastic material is preferably used in the formation of the preferred embodiment, it will be understood that materials that are compatible with one another but have differing degrees of hardness may be injection molded into the sprues 170–200. In the case where VESTAMID E Series polyether block copolyamides (PEBA) supplied by HULS AMERICA, Inc., are employed, a series of PEBA blends(VESTAMID E Series) are available in 35 D, 40D, 55D, 63D, 70D, and 72D, Shore hardness, for example. The performance characteristics of these thermoplastic elastomers rank between the performance of relatively soft and flexible synthetic rubber and relatively hard and rigid Nylon 12.

For example, a softer or more flexible material, e.g., a Shore 35 D, Shore 40 D or Shore 55D PEBA can be injected through the sprues 180–190 to customize the flexibility of the strain relief coil 65. A second, harder material, e.g., Shore 63 D PEBA or Shore 70 D PEBA can be injected through the sprues 170 and 175 to form the hub portion 90 with desirable dimensional stability and hardness particularly at the hub fitting 95.

Moreover, the two materials may be blended together to provide a progressively increasing flexibility extending distally through the length of the strain relief coil 65. The softest blend, e.g., Shore 35 PEBA can be injected through distal sprue 180, a harder blend, e.g., Shore 55 PEBA can be injected through proximal sprue 190, and an intermediate blend, e.g., Shore 40 PEBA, or another blend can be injected through the intermediate sprue 185. In addition, the compatible thermoplastic materials of differing hardness can be injected through sprues 170,175 and 195, 200. An intermediate hardness blend, e.g. Shore 55 or Shore 63 PEBA can be injected through sprues 170,175 to form the solid, tapered proximal portion of the catheter hub/body junction 70 and proximally toward the hub fitting 95. The hardest blend, e.g., Shore 70 or 72 PEBA can be injected through the sprues 195 and 200 to form the hub fitting 95 to assure its dimensional rigidity for fitting with other equipment and providing a dimensionally stable hub lumen end opening 105.

These mixtures of thermoplastic materials and blends thereof can all be of the same color or be of differing colors to show the distally increasing or graduated softness and distally increasing flexibility of the unitary catheter hub and stain relief 60, particularly along the length of the catheter hub/body junction 70.

The above described method and a single thermoplastic material (VESTAMID E40-S3) of modulus 100,000 psi (approximately) was employed to form a unitary catheter hub and strain relief 60 on a catheter body 15 as described above and depicted in the figures. The overall length of the unitary catheter hub and strain relief 60 is about 2.024 inches, including a strain relief coil length of about 0.644 inches and a catheter hub/body junction 70 length of about 1.034 inches. The proximal and distal spiral coil diameters are about 0.258 inches and about 0.190 inches, respectively. The catheter body 15 is formed as described above in reference to FIGS. 3–5 having an outer diameter of about 0.106 inches and a hoop strength of about four pounds. The adjacent spiral coil turns 150 of the spiral strain relief coil 65 were spaced from one another and adhered to the exterior surface of the outer tubular sheath 125 of the catheter body 15.

The use of the materials identified above and the spiral coil shape of the strain relief coil 65 provide the ability to bend the strain relief coil 65 and the underlying catheter body 15 into an arc of 180° over the length of the catheter hub/body junction 70 and a further exposed length of about one inch of the proximal region 30 before a kink was induced. This represents an improvement of about 90%–100% of the bending arc achieved using a like dimensioned strain relief formed of a constant diameter tube formed of polyvinyl chloride.

The use of the strain relief coil 65 with spaced coil turns of a single coil decreasing in diameter distally provides superior flexibility and increases resistance to kinking of the catheter body 15 over the catheter hub/body junction 70 and distally to the distal strain relief coil end 80. The flexibility is uniform around the full 360° circumference of the catheter body at all points along the length of the strain relief coil 65.

The injection method of the present invention also eliminates the need to separately fabricate, assemble and glue the parts of the hub and strain relief to the catheter body proximal end. However, it will be understood that many of the performance advantages of the unitary catheter hub and strain relief 60 can also be achieved by injection molding the unitary catheter hub and strain relief 60 a separate piece and attaching it to the proximal portion of the catheter body 15 as illustrated in FIG. 2. In this manufacturing method, a straight mandrel of slightly larger diameter can be substituted for the catheter body 15 within the mold cavity 165 while the molten material is injected. The straight mandrel can then be withdrawn after the molded unitary catheter hub and strain relief 60 is ejected resulting in the strain relief coil lumen 85 and a lumen extending proximally through the length of the catheter/hub body junction 70. The catheter body proximal end 55 is inserted into that lumen and adhesive or heat may be applied to retain it therein.

However, this approach does not offer the cost reduction advantages attendant to molding the unitary catheter hub and strain relief 60 over the proximal portion of the catheter body 15 as described above in reference to FIG. 8.

It will also be understood that the strain relief coil 65 can be manufactured by any of the above described methods to have a wide range of lengths and coil turns and tapers. In addition, although only a single lumen medical vascular catheter 10 is described and depicted in the drawings, it will be understood that the present invention may be practiced and implemented to provide such a strain relief for a wide variety of such catheters. For example, the present invention may be practiced and implemented to provide such a strain relief coil in substitution for the stain reliefs incorporated in the above-described prior art catheters although not all of the benefits of the preferred embodiment may be realized.

The preceding specific embodiments are illustrative of the practice of the invention. It is to be understood, however, that other expedients known to those skilled in the art or disclosed herein, may be employed without departing from the scope of the appended claims.

PARTS LIST FOR FIGS. 1–9

No. Component 10 medical vascular catheter
15 catheter body
20 catheter body side wall
25 catheter lumen
30 proximal region
35 transition region
40 distal region
45 distal lumen end opening
50 catheter body distal end
55 catheter body proximal end
60 unitary catheter hub and strain relief
65 strain relief coil
70 catheter hub/body junction
75 proximal strain relief coil end
80 distal strain relief coil end
85 strain relief coil lumen 90 hub portion
95 hub fitting
100 hub lumen
105 hub lumen end opening
110 distal hub lumen portion
115 hubflat
120 hub flat
125 inner tubular sheath
130 outer tubular sheath
135 wire braid tube
140 warp wire filament pair
145 woof wire filament pair
150 spiral coil turns
155 injection mold
160 tubular mandrel
165 mold cavity
170–200 injection sprues
205 spiral turn section
210 spiral heating element turns
215 distal extension

What is claimed is:

1. A medical vascular catheter adapted to be inserted into a blood vessel from an incision through the skin of a patient for introducing other devices or fluids for diagnostic or therapeutic purposes into the patient's vasculature, said catheter comprising:

an elongated catheter body enclosing a catheter lumen and extending between a catheter body proximal end and a catheter body distal end, the catheter body having a catheter body side wall formed at least in part of a thermoplastic material; and a unitary catheter hub and strain relief formed of a thermoplastic hub material receiving and adhered to a proximal portion of said catheter body in an elongated catheter hub/body junction thereof, said unitary catheter hub and strain relief having a proximal hub portion and a strain relief coil formed integrally with a distal end of said proximal hub portion and extending distally therefrom in a coil length between a proximal strain relief coil end and a distal strain relief coil end and surrounding a strain relief coil lumen receiving said proximal portion of said catheter body, said proximal hub portion having a distal hub lumen portion aligned axially with said strain relief coil lumen for receiving said proximal portion of said catheter body in an elongated catheter hub/body junction, said strain relief coil formed of a plurality of spiral turns separated from one another by an interleaved spiral-shaped spacing and providing a uniform bending flexibility around the 360° circumference of the catheter body that increases distally through the length of said strain relief coil.

2. The medical vascular catheter of claim 1, wherein said proximal portion of said catheter body has a side wall crush resistance of about 2–7 pounds.

3. The medical vascular catheter of claim 1, wherein said proximal portion of said catheter body is formed of an outer tubular sheath, an inner tubular sheath and a wire braid tube sandwiched between the outer and inner tubular sheathes.

4. The medical vascular catheter of claim 3, wherein said outer tubular sheath is formed of a thermoplastic material selected from the group comprising polyamides, polyether block copolyamides (PEBA), polyurethanes, silicone rubbers, nylons, polyethylenes, and fluorinated hydrocarbon polymers having a first Shore hardness.

5. The medical vascular catheter of claim 4, wherein:

said unitary catheter hub and strain relief is formed of a thermoplastic material selected from said group comprising polyamides, polyether block copolyamides (PEBA), polyurethanes, silicone rubbers, nylons, polyethylenes, fluorinated hydrocarbon polymers, the selected thermoplastic material having the capability of thermally bonding with the thermoplastic material selected to form the outer tubular sheath.

6. The medical vascular catheter of claim 5, wherein the selected thermoplastic material used to form said unitary catheter hub and strain relief has a second Shore hardness that equals or exceeds said first Shore hardness.

7. The medical vascular catheter of claim 6, wherein said strain relief coil has a progressively increasing flexibility extending distally through said coil length of said strain relief coil from said proximal hub portion to said distal strain relief coil end.

8. The medical vascular catheter of claim 3, wherein:

said outer tubular sheath is formed of a thermoplastic material selected from the group comprising polyamides, polyether block copolyamides (PEBA), polyurethanes, silicone rubbers, nylons, polyethylenes, fluorinated hydrocarbon polymers having a first Shore hardness;

said strain relief coil is formed of a thermoplastic material selected from said group comprising polyamides, polyether block copolyamides (PEBA), polyurethanes, silicone rubbers, nylons, polyethylenes, fluorinated hydrocarbon polymers, the selected thermoplastic material having the capability of thermally bonding with the thermoplastic material selected to form the outer tubular sheath, said selected thermoplastic material used to form said strain relief coil having a Shore hardness equaling or exceeding said first Shore hardness; and said proximal hub portion is formed integrally with said strain relief coil and of said selected material used to form said strain relief coil but having a third Shore hardness exceeding said second Shore hardness, whereby said proximal hub portion is harder and more rigid than said strain relief coil.

9. The medical vascular catheter of claim 8, wherein said strain relief coil has a progressively increasing flexibility extending distally through the length of the strain relief coil from said proximal hub portion which is effected at least in part by forming said strain relief coil of blends of said selected one of said thermoplastic materials exhibiting progressively decreasing Shore hardness distally from the integral junction with said proximal hub portion.

10. The medical vascular catheter of claim 1, wherein said proximal portion of said catheter body is formed of a thermoplastic material selected from the group comprising polyamides, polyether block copolyamides (PEBA), polyurethanes, silicone rubbers, nylons, polyethylenes, and fluorinated hydrocarbon polymers having a first Shore hardness.

11. The medical vascular catheter of claim 10, wherein:

said unitary catheter hub and strain relief is formed of a thermoplastic material selected from said group comprising polyamides, polyether block copolyamides (PEBA), polyurethanes, silicone rubbers, nylons, polyethylenes, fluorinated hydrocarbon polymers, the selected thermoplastic material having the capability of thermally bonding with the thermoplastic material selected to form the proximal portion of said catheter body.

12. The medical vascular catheter of claim 11, wherein said strain relief coil has a progressively increasing flexibility extending distally through said coil length of said strain relief coil from said proximal hub portion to said distal strain relief coil end.

13. The medical vascular catheter of claim 10, wherein said unitary catheter hub and strain relief is formed of a thermoplastic material selected from said group comprising polyamides, polyether block copolyamides (PEBA), polyurethanes, silicone rubbers, nylons, polyethylenes, fluorinated hydrocarbon polymers, the selected thermoplastic material having a second Shore hardness that equals or exceeds said first Shore hardness and having the capability of thermally bonding with the thermoplastic material selected to form the proximal portion of said catheter body.

14. The medical vascular catheter of claim 13, wherein said strain relief coil has a progressively increasing flexibility extending distally through said coil length of said strain relief coil from said proximal hub portion to said distal strain relief coil end.

15. The medical vascular catheter of claim 1, wherein:

said proximal portion of said catheter body is formed of a thermoplastic material selected from the group comprising polyamides, polyether block copolyamides (PEBA), polyurethanes, silicone rubbers, nylons, polyethylenes, fluorinated hydrocarbon polymers having a first Shore hardness;

said strain relief coil is formed of a thermoplastic material selected from said group comprising polyamides, polyether block copolyamides (PEBA), polyurethanes, silicone rubbers, nylons, polyethylenes, fluorinated hydrocarbon polymers, the selected thermoplastic material having the capability of thermally bonding with the thermoplastic material selected to form the proximal portion of said catheter body, said selected thermoplastic material used to form said strain relief coil having a Shore hardness equaling or exceeding said first Shore hardness; and said proximal hub portion is formed integrally with said strain relief coil and of said selected material used to form said strain relief coil but having a third Shore hardness exceeding said second Shore hardness, whereby said proximal hub portion is harder and more rigid than said strain relief coil.

16. The medical vascular catheter of claim 15, wherein said strain relief coil has a progressively increasing flexibility extending distally through the length of the strain relief coil from said proximal hub portion which is effected at least in part by forming said strain relief coil of blends of said selected one of said thermoplastic materials exhibiting progressively decreasing Shore hardness distally from the integral junction with said proximal hub portion.

17. The medical vascular catheter of claim 10, wherein the selected thermoplastic material used to form said unitary catheter hub and strain relief has a second Shore hardness that equals or exceeds said first Shore hardness.

18. The medical vascular catheter of claim 17, wherein said strain relief coil has a progressively increasing flexibility extending distally through said coil length of said strain relief coil from said proximal hub portion to said distal strain relief coil end.

19. The medical vascular catheter of claim 1, wherein said strain relief coil has a progressively increasing flexibility extending distally through the length of the strain relief coil from said proximal hub portion to said distal strain relief coil end.

20. The medical vascular catheter of claim 19, wherein said plurality of spiral turns of said strain relief coil have outer diameters that decrease from the junction with said proximal hub portion and the distal strain relief coil end.

21. A catheter comprising:

an elongated catheter body having a proximal portion; and a unitary catheter hub and strain relief formed of a thermoplastic hub material receiving a proximal portion of said catheter body in an elongated catheter hub/body junction thereof, said unitary catheter hub and strain relief having a proximal hub portion and a strain relief coil formed integrally with a distal end of said proximal hub portion and extending distally therefrom in a coil length between a proximal strain relief coil end and a distal strain relief coil end and surrounding a strain relief coil lumen receiving said proximal portion of said catheter body, said proximal hub portion having a distal hub lumen portion aligned axially with said strain relief coil lumen for receiving said proximal portion of said catheter body in the elongated catheter hub/body junction, said strain relief coil formed of a plurality of spiral turns separated from one another by an interleaved spiral-shaped spacing and providing a universal bending flexibility of the catheter body that increases distally through the length of said strain relief coil.

* * * * *